US00PP12276P2

(12) United States Plant Patent
Vandenberg

(10) Patent No.: US PP12,276 P2
(45) Date of Patent: Dec. 11, 2001

(54) CHRYSANTHEMUM PLANT NAMED 'RASPBERRY YOLOMPOC'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,658

(22) Filed: Mar. 15, 2000

(51) Int. Cl.[7] ..... A01H 5/00
(52) U.S. Cl. ..... Plt./286
(58) Field of Search ..... Plt./286, 297, 298

(56) References Cited

U.S. PATENT DOCUMENTS 4,616,099 * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4):138–142.*
Broertjes, et al., 1980, "A mutant of mutant of a . . . Irradiation of progressive radiation induced mutants in a mutation breeding programme with *Chrysanthemum morifolium*", Ezphytica, 29:525–530.*
Gosling, ed., 1979, "The Chrysanthemum Manual—6$^{th}$ edition", The National Chrysanthemum Society, London, Essex Telegraph Press, Ltd., pp. 329–336.*
Broertjes, et al., 1978, "Application of Mutation Breeding Methods In the Improvement of Vegetatively Propagated Crops", Elsevier Sci. Pub. Co., New York, pp. 162–175.*
Searle, et al., 1968, "Chrysanthemums the year Round", Blanford Press, London, pp. 27–29, 320–327.*
Chan, 1966, "Chrysanthemum and rose mutations induced by x–rays", Am. Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in chrysanthemum using x– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Raspberry Yolompoc', characterized by its upright, outwardly spreading and uniformly mounded plant habit; freely branching, dense and full plants; dark green foliage; uniform flowering; early flowering, eight-week response time; very freely flowering with about nine inflorescences per lateral stem; daisy-type inflorescences that are about 6.3 cm in diameter; rich reddish purple-colored ray florets and bright yellow disc florets; and excellent postproduction longevity with inflorescences and leaves maintaining good substance and color for at least three weeks in an interior environment.

2 Drawing Sheets

BLACKGROUND OF THE INVENTION

The present Invention relates to a new and distinct cultivar of Chrysanthemum plant, botanically known as *Dendranthema grandiflora* and hereinafter referred to by the cultivar name Raspberry Yolompoc.

The new Chrysanthemum is a product of a mutation induction breeding program conducted by the Inventor in Fort Myers, Fla. and Salinas, Calif. The objective of the program is to create new Chrysanthemum cultivars with desirable inflorescence form and floret colors, good substance, and excellent post-production longevity.

The new Chrysanthemum originated by exposing unrooted cuttings of the Chrysanthemum cultivar Yolompoc, disclosed in U.S. Plant Pat. No. 11,203, to X-ray radiation in September, 1996, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in April, 1997. The selection of this plant was based on its desirable inflorescence form and ray floret color.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Raspberry Yolompoc has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Raspberry Yolompoc'. These characteristics in combination distinguish 'Raspberry Yolompoc' as a new and distinct Chrysanthemum:

1. Upright, outwardly spreading and uniformly mounded plant habit.
2. Freely branching, dense and full plants.
3. Dark green foliage.
4. Uniform flowering.
5. Early flowering, eight-week response time.
6. Very freely flowering; about nine inflorescences per lateral stem.

7. Daisy-type inflorescences that are about 6.3 cm in diameter.

8. Rich reddish purple-colored ray florets and bright yellow disc florets.

9. Excellent postproduction longevity with inflorescences and leaves maintaining good substance and color for at least three weeks in an interior environment.

Compared to plants of the parent cultivar, Yolompoc, ray florets of plants of the new Chrysanthemum are more red in color than ray florets of plants of the cultivar Yolompoc. In addition, plants of the new Chrysanthemum flower about two or three days later than plants of the cultivar Yolompoc.

Compared to plants of the cultivar Regal Yolompoc, U.S. Plant patent application Ser. No. 09/525,659, filed concurrently with this application, ray florets of plants of the new Chrysanthemum are more red and slightly lighter in color than ray florets of plants of the cultivar Regal Yolompoc.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a side perspective view of a typical flowering plant of 'Raspberry Yolompoc'.

The photograph at the bottom of the first sheet comprises a close-up view of upper (left) and lower (right) surfaces of typical inflorescences and upper (left) and lower (right) surfaces of typical leaves of the cultivar Raspberry Yolompoc.

The photograph at the top of the second sheet comprises a side perspective view of typical flowering plants of 'Raspberry Yolompoc' (left) and 'Yolompoc' (right).

The photograph at the bottom of the second sheet comprises a close-up view of typical inflorescences of plants of 'Raspberry Yolompoc' (left) and 'Yolompoc' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Leamington, Ontario, Canada, under greenhouse conditions which approximate those generally used in commercial potted Chrysanthemum production. Four unrooted cuttings were directly stuck in a 15-cm container and pinched once. Plants used for this description were grown as center budded-types. Measurements and numerical values represent averages of typical flowering plants.

Botanical classification: *Dendranthema grandiflora* cultivar Raspberry Yolompoc.

Commercial classification: Daisy center budded-type potted Chrysanthemum.

Parentage: Induced mutation of the *Dendranthema grandiflora* cultivar Yolompoc, disclosed in U.S. Plant Pat. No. 11,203.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Herbaceous daisy potted Chrysanthemum typically grown as a center budded-type. Inverted triangle; stems upright and outwardly spreading giving a uniformly mounded appearance to the plant. Freely branching; about three to four lateral branches develop after removal of terminal apex (pinching); dense and full plants.

*Plant height*.—About 29 cm.

*Plant width*.—About 47 cm.

*Foliage description*.—Arrangement: Alternate. Length: About 7 cm. Width: About 4.9 cm. Apex: Cuspidate. Base: Cuneate to truncate. Margin: Palmately lobed, sinuses between lateral lobes mostly divergent. Texture: Upper and lower surfaces with very fine pubescence; veins prominent on lower surface. Petiole length: About 2.1 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance*.—Daisy inflorescence form with elongated oblong-shaped ray florets. Inflorescences borne on terminals above foliage. Disk and ray florets arranged acropetally on a capitulum.

*Flowering respeonse*.—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity*.—Inflorescences and leaves maintain good color and substance for at least three weeks in an interior environment.

*Quantity of inflorescences*.—Very freely flowering; about nine inflorescences per lateral stem and about 30 inflorescences per plant.

*Inflorescence bud*.—Height: About 6 mm. Diameter: About 7 mm. Color: Close to 143A.

*Inflorescence size*.—Diameter: About 6.3 cm. Depth (height): About 1.4 cm. Diameter of disc: About 1.4 cm.

*Ray florets*.—Shape: Elongated-oblong. Orientation: Initially upright, then about 20 to 25° to horizontal. Length: About 3 cm. Width: About 8.5 mm. Apex: Rounded to emarginate. Margin: Entire. Texture: Smooth, glabrous, satiny. Number of ray florets per inflorescence: About 22. Color: When opening: Close to 60B. Fully opened, upper surface: Close to 60B; flower color may appear darker under cool temperatures and lighter under high light and warm temperatures. Fully opened, lower surface: Close to 58A.

*Disc florets*.—Shape: Tubular. Apex: Serrated. Length: About 5.5 mm. Width: Apex: About 1.5 mm. Base: About 1 mm. Number of disc florets per inflorescence: About 92. Color: Immature: 144A to 154A. Mature: Apex: Yellow, 7A to 9A. Mid-section: White, 155D, or very light green, 145A to 145B. Base: White, 155D.

*Peduncles*.—Aspect: Angled about 40° to stem. Length: First peduncle: About 3.5 cm. Fourth peduncle: About 6.4 cm. Diameter: About 2.5 mm. Texture: Pubescent. Color: 146A.

*Reproductive organs*.—Androecium: Present on disc florets only. Anther color: 7A. Pollen amount: Scarce. Pollen color: 9A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Raspberry Yolompoc', as illustrated and described.

* * * * *

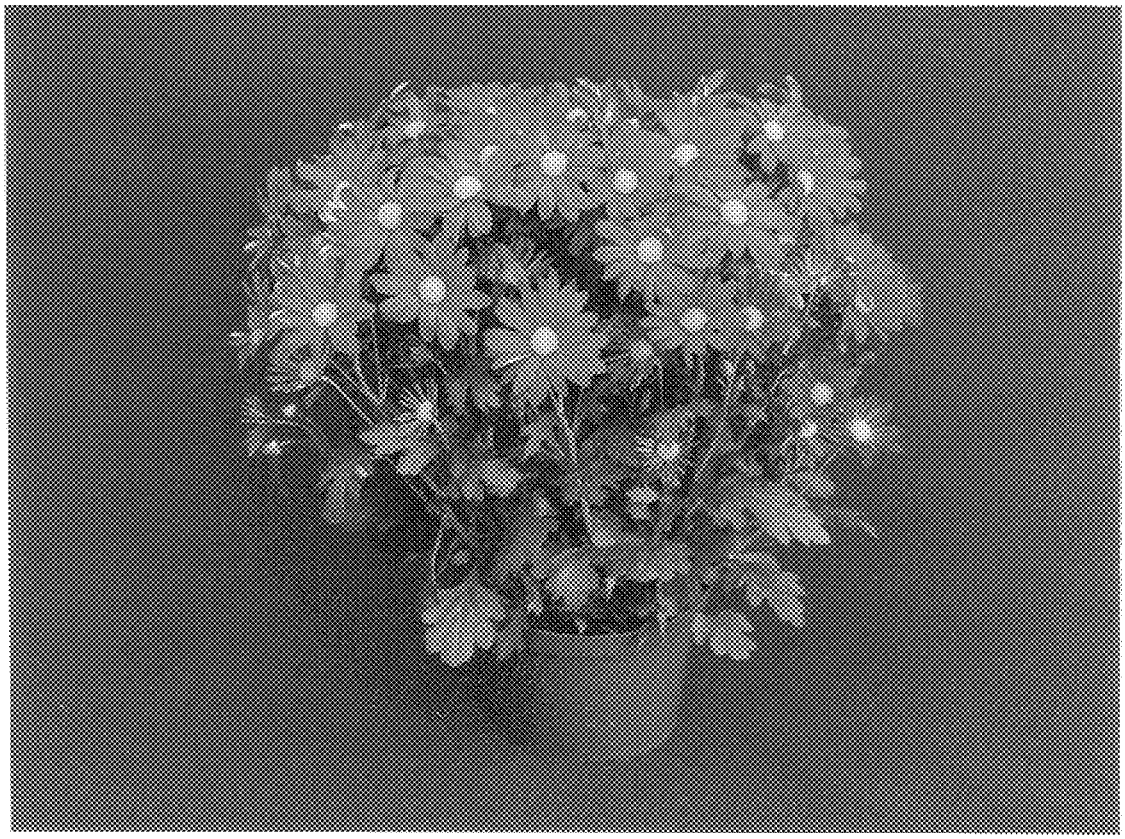
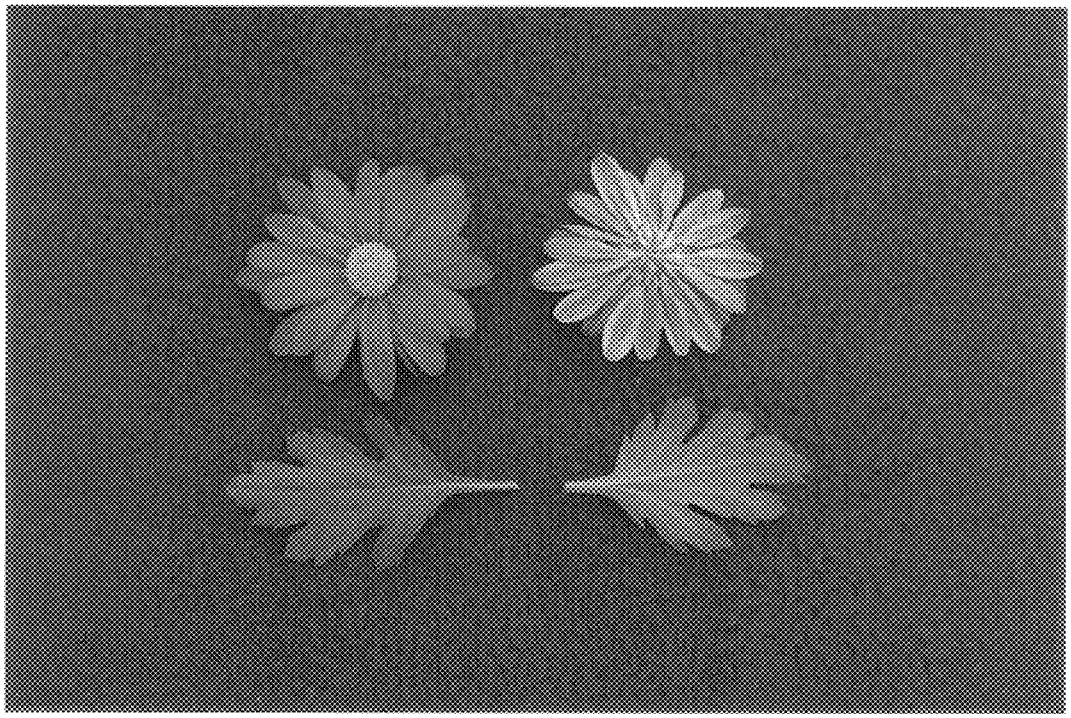

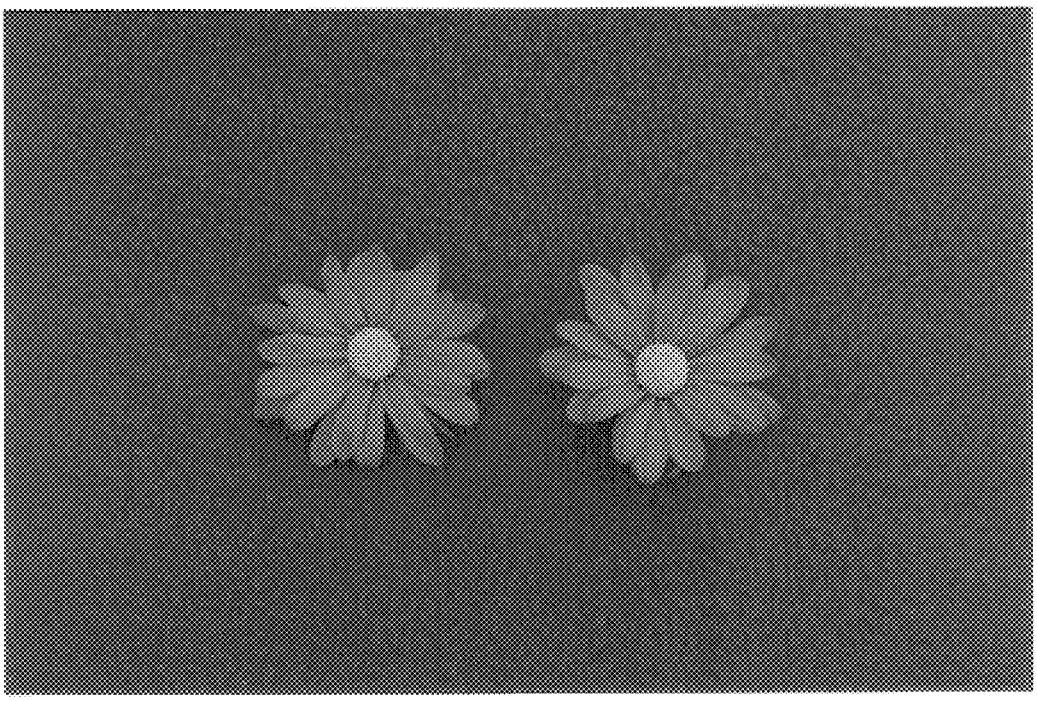

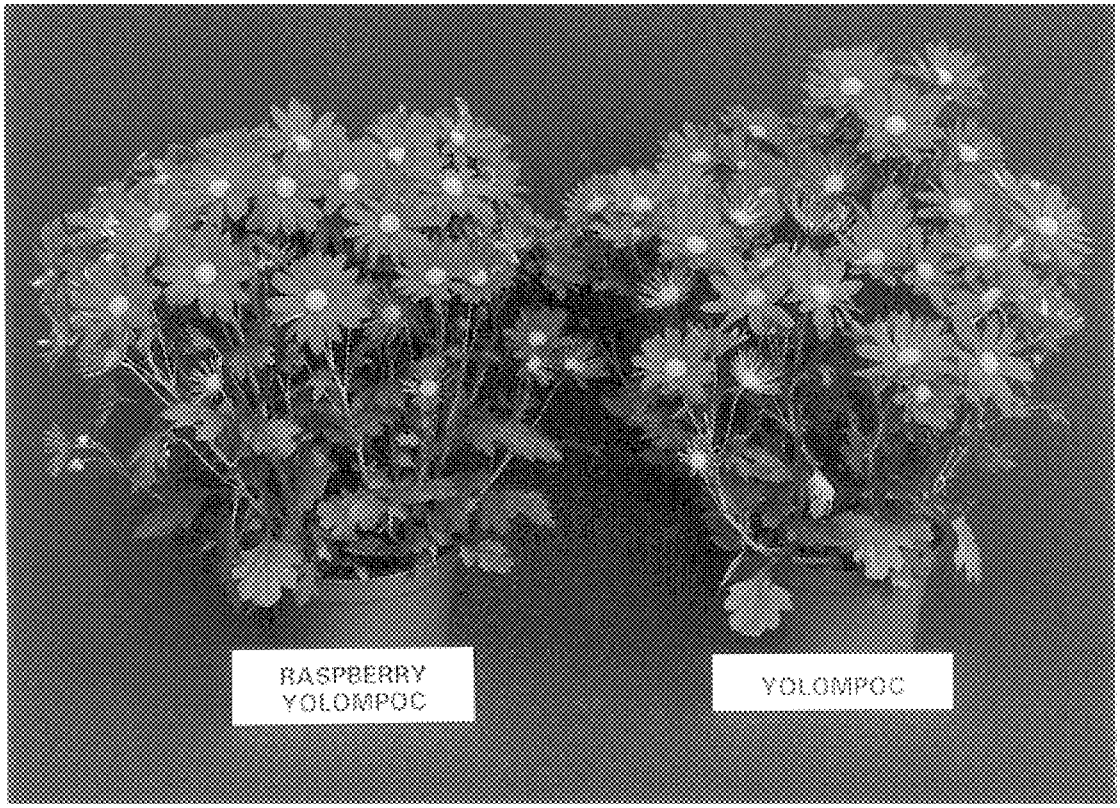
RASPBERRY
YOLOMPOC
YOLOMPOC